(12) United States Patent
Rida (10) Patent No.: US 8,142,892 B2
(45) Date of Patent: Mar. 27, 2012

(54) TAILORED MAGNETIC PARTICLES COMPRISING A NON-MAGNETIC COMPONENT AND A MAGNETIC CORE-SHELL COMPONENT, AND METHOD TO PRODUCE SAME

(75) Inventor: Amar Rida, Chavannes-Renens (CH)

(73) Assignee: Spinomix S.A., Lausanne (CH)

( * ) Notice: Subject to any disclaimer, the term of this patent is extended or adjusted under 35 U.S.C. 154(b) by 757 days.

(21) Appl. No.: 11/720,232

(22) PCT Filed: Nov. 23, 2005

(86) PCT No.: PCT/EP2005/056178
§ 371 (c)(1),
(2), (4) Date: May 25, 2007

(87) PCT Pub. No.: WO2006/056579
PCT Pub. Date: Jun. 1, 2006

(65) Prior Publication Data
US 2008/0014442 A1 Jan. 17, 2008

(30) Foreign Application Priority Data

Nov. 25, 2004 (EP) .................................... 04106094

(51) Int. Cl.
*A61K 9/28* (2006.01)
*A61K 9/54* (2006.01)
*B32B 5/16* (2006.01)
(52) U.S. Cl. ......... 428/403; 424/417; 424/474; 424/490
(58) Field of Classification Search .................. 428/403; 424/417, 474, 490
See application file for complete search history.

(56) References Cited

U.S. PATENT DOCUMENTS
3,958,068 A * 5/1976 Umeki et al. ................. 428/403
(Continued)

FOREIGN PATENT DOCUMENTS
WO WO90/15666 12/1990
(Continued)

OTHER PUBLICATIONS

Seip CT et al: "The fabrication and organization of self-assembled metallic nanoparticles formed in reverse micelles" Nanostructured Materials, Elsevier, New York, NY, US vol. 12. No. 1-4, 1999, pp. 183-186.

(Continued)

*Primary Examiner* — Hoa (Holly) Le
(74) *Attorney, Agent, or Firm* — Sturm & Fix LLP (57) ABSTRACT

Bio-functionalized magnetic particles have a non-magnetic material matrix which supports core/shell magnetic elements composed from a ferromagnetic core material and a shell material. The shell material can be chosen either among an antiferromagnetic material, a ferromagnetic material of a kind different from the core ferromagnetic material or a metal material. By a proper choice of materials and dimension tuning of both the core and the shell as well as the amount and the concentration of the magnetic elements within the non-magnetic matrix, the bio-functionalized magnetic particles is tailored to exhibit an enhanced magnetic energy. When subjected to an alternating magnetic field, the magnetic particles exhibit specific rotational dynamics in correspondence with the amplitude and the frequency of the applied magnetic filed. Aggregation structures of the magnetic particles are controlled and manipulated by the alternating magnetic field. The magnetic particles are functionalized by specific ligands for the probing and manipulating of biomolecules and chemical substances.

16 Claims, 5 Drawing Sheets

U.S. PATENT DOCUMENTS

| | | | |
|---|---|---|---|
| 5,607,768 A * | 3/1997 | Lee | 428/403 |
| 5,648,124 A | 7/1997 | Sutor | |
| 5,932,097 A | 8/1999 | Wilson | |
| 6,045,925 A * | 4/2000 | Klabunde et al. | 428/548 |
| 6,514,481 B1 * | 2/2003 | Prasad et al. | 424/9.32 |
| 6,773,812 B2 * | 8/2004 | Chandler et al. | 428/403 |
| 7,147,916 B2 * | 12/2006 | Iwasaki et al. | 428/403 |
| 7,232,691 B2 * | 6/2007 | Kraus et al. | 436/526 |
| 7,282,540 B2 * | 10/2007 | Ozaki et al. | 525/244 |
| 7,741,120 B2 * | 6/2010 | Klimov et al. | 436/56 |
| 2002/0187504 A1 | 12/2002 | Reich | |
| 2004/0216810 A1 | 11/2004 | Iwasaki | |

FOREIGN PATENT DOCUMENTS

WO    WO03004151    1/2003

OTHER PUBLICATIONS

Skumryev Vassil et al: "Beating the superparamagnetic limit with exchange bias." Nature. Jun. 19, 2003. vol. 423, No. 6942. pp. 850-853.

* cited by examiner

TAILORED MAGNETIC PARTICLES COMPRISING A NON-MAGNETIC COMPONENT AND A MAGNETIC CORE-SHELL COMPONENT, AND METHOD TO PRODUCE SAME

FIELD OF THE INVENTION

The invention generally relates to magnetic particles for which magnetic properties are tailored to provide a specific response when a fluid suspension of the particles is subjected to an external magnetic field. More precisely, the invention concerns a method of preparing magnetic particles with specific magnetic properties and a method of manipulating them with a magnetic field. Further, the invention relates to the use of magnetic particles of the above kind for assaying, manipulation and purification of biomolecules and chemical substances. The particles are magnetic in the sense that they are capable of being magnetised in the presence of a magnetic field even though they are not themselves magnetic in the absence of a magnetic field.

STATE OF THE ART

Nowadays magnetic responsive particles are widely known and used as solid phase support for biological and chemical analysis. For instance, the magnetic particles surface can be activated to carry a probe that specifically interacts with complementary target molecules. The advantage of using magnetic particles is that they can be simply manipulated using a magnetic field to control the reaction on their surface and/or to separate the specific target molecule from the initial "contaminant" surrounding medium. Magnetic particle based procedures and systems are relatively rapid, easy and require simple equipment.

Several methods of synthesizing magnetic responsive particles and manipulating them have been developed during the last decades. Generally, preparation of magnetic particles consists in the encapsulation or incorporation of primary magnetic responsive particles in a non-magnetic matrix such as polymer a glass. For example in patent application WO90/15666 magnetic fine particles are coated with a polymeric material. More recently WO03/004151 disclosed the incorporation of magnetic fine particles in a core of polymeric particles. Rather than encapsulating magnetic substances in a core matrix, U55648124 disclosed the use of spherical particles as supports for deposition of smaller magnetite particles to provide core-shell magnetic responsive particles.

One of the most important concerns in synthesizing magnetic particles like those described above, is to provide magnetic responsive particles (paramagnetic particles) with a minimum of residual magnetisation (supraparamagnetic particles). Such consideration is important in order to minimize the agglomeration of magnetic particles during the manipulation process with a magnetic field. Indeed, the separation and manipulation of magnetic particles in liquid suspension necessitates the application of a "large" magnetic field and magnetic field gradient. In such conditions, monodispersed magnetic particles agglomerate under the influence of their mutual magnetic dipole interaction. Recovering a monodispersed magnetic particles suspension after magnetic field removal necessitates, therefore, a low residual dipolar magnetization of the particles. For this reason, finer magnetic particles (known also as ferrofluid suspensions) are used as primary magnetic material. In fact, when using finer magnetic particles as primary magnetic material, the direction of the residual magnetization of the fine particles is so small that it can be reversed by the surrounding thermal energy fluctuations, leading to a vanishing average residual magnetisation.

Supraparamagnetic particles are widely available on the market. They are known to be stable and highly monodispersed particles. However, one serious limitation associated with the above technologies is that magnetic particles present a low magnetic susceptibility due to the finer magnetic primary material. In this case, a high magnetic field is necessary to create a sufficient magnetic force to manipulate these particles. Moreover, magnetic particles (beads) of the above kind do not lend themselves to controlling and adapting their magnetic proprieties for specific applications, for instance obtaining different responses in correspondence with the applied magnetic field.

To deal with such issues, new kinds of magnetic particles are proposed in U55932097 and more recently in U52002/0187504A1. In U55932097, laminar shaped magnetic particles composed from the superposition of layers of ferromagnetic (pre-polarised) and antiferromagnetic materials, which layers are separated by a nonmagnetic spacer layer, are proposed. In this case, the magnetic exchange force between the ferromagnetic and antiferromagnetic layers is exploited to pin the magnetic moment of the ferromagnetic layer(s) in a specific direction depending on the applied magnetic field. In this way, different magnetic particles with different magnetic moments in response to a predetermined external magnetic field are obtained. U52002/0187504A1 discloses magnetic nanowires which are elongated magnetic entities obtained by successive deposition of different magnetic and non-magnetic layers. One of the advantages of such new kinds of particles is the possibility to be tailored by adjusting the deposited layer to obtain different magnetic particles with different magnetic moments. However, controlling the aggregation and effectively manipulating such elongated and laminar shape particles remains a non-cleared up question.

In this spirit it would be important to have available magnetic particles for which magnetic properties can be tailored to provide a specific response to an applied magnetic field. Moreover, it would be of benefit to synthesize new magnetic particles with specific magnetic properties that can be effectively controlled and manipulated. Also, having an effective control of the aggregation structures of magnetic particles during their manipulation remains an unsolved problem.

SUMMARY OF THE INVENTION

Accordingly, the first aspect of invention concerns magnetic responsive particles and a method for preparing them.

Accordingly, the second aspect of the invention is to provide a method of manipulating the said magnetic particles.

Accordingly, the third aspect of the invention discloses a method of using the magnetic particles prepared and manipulated following the previous aspects in life science and particularly for assaying, manipulation and purification of biomolecules and chemical substances.

Different embodiments are set out in the detailed description.

The first aspect of the invention provides a bio-chemically active magnetic particle for use in a magnetic particle fluid suspension for selectively binding with at least one target molecule, the particle comprising (a) a non-magnetic component; (b) a core/shell magnetic component; and (c) an external coating designed to allow an affinity recognition for selectively binding the particle with at least one target molecule. The particular features of this first particle are: that its magnetic component (b) comprises a ferromagnetic core material and shell material; the shell materials can be chosen either among an antiferromagnetic material, a ferromagnetic material of a kind different from the core ferromagnetic material or transition metal material; the Néel temperature of the antiferromagnetic phase is above 300 K; the ferromagnetic core material comprises at least one fine ferromagnetic particle having zero coercive field or a given coercive field; and the fine ferromagnetic particle(s) is associated with the shell material to enhance the magnetic energy and to provide the particle with a coercive field much greater than that of the fine ferromagnetic particle(s). The coercive field of the particle according to the invention will generally be greater than 100 Oersted (Oe) at 300 K, usually above 200 (Oe) and preferably greater than 400 (Oe).

Our objective in associating a shell material and a ferromagnetic core material is to increase the coercive field of the particle compared to the case where the particle is composed only of the ferromagnetic material. Indeed, the primary magnetic element in our invention is a 'fine" ferromagnetic particle which has a zero coercive field or a given (usually low) coercive field and even behaves as a superparamagnetic at ordinary temperature. The idea is to put such ferromagnetic fine particle in association with a shell material, usually by direct contacting the two, to enhance the coercive field of the overall particle, due to the magnetic exchange coupling between the core and the shell. For example if we consider a Nickel (Ni) magnetic particle of 10 nm diameter the coercive field of this particle is about 10 (Oe) at 300 K which is very low and the particle is substantially superparamagnetic at ordinary temperature. However, if we coat this particle with a layer of Nickel oxide (NiO) (which is an antiferromagnetic material) of 5 nm thickness the coercive field increases to a value of about 250 (Oe). A similar effect is obtained with core/shell magnetic fine particles composed from a ferromagnetic core and magnetic metal shell such as $Fe_2O_3/C0$ fine particles. Further, a similar effect is obtained by considering core/shell bi-magnetic fine particles composed from a ferromagnetic core and ferromagnetic shell material of a kind different from the core ferromagnetic material such as $FePt/Fe_2O_3$, $Co/Fe_2O_3$ or $SmCo_5/Fe_2O_3$ fine particles. So, the particle of the invention comprises at least one primary ferromagnetic fine particle that is associated with (in particular in contact with) a shell material to provide an enhanced coercive field. In the first aspect of the invention, the above-mentioned primary responsive particles are ferromagnetic fine particles. The ferromagnetic material includes, but is not limited to, Cobalt (Co), Nickel (Ni), magnetite (y-$Fe_2O_3$) or any alloy thereof. Some ferromagnetic alloys having a high magnetisation and strong axial magnetocrystalline anisotropy, such as, Pt, FePt, $PrCo_5$, Sm and CoPt, are preferably used to provide a high coercive field. In general transition metals, metals oxides and their alloys are preferred materials entering in the composition of the core/shell magnetic component. In the step of preparing the magnetic particles according to the invention a magnetic a heat annealing step is preferred to adjust and increase the coercive field. The size of the fine ferromagnetic core which determines the magnetic response of the particles is preferably less than the critical size (i.e. the size above which the particle becomes a multi-domain particle) of a single magnetic domain. Indeed, the size of the fine particles entering in the composition of the ferromagnetic core is in the nanometric size between 500 or 200 to 1 nm and preferably between 50 or 25 to 5 nm. Further, it is preferable that ferromagnetic fine particles have acicular shape to increase the magnetic anisotropy and thus the coercive field.

A method of preparing magnetic particles with a defined coercive field, according to the first aspect of the invention, comprises the steps of:

1. Providing primary magnetic responsive fine particles having zero coercive field or a defined coercive field;
2. Integrating the primary fine particles of step 1) in a non-magnetic support to provide a secondary core particle;
3. Adjusting the coercive field of the secondary particle by controlling the amount and the concentration of the primary fine particles provided in step 1) and integrated following step 2); and
4. Functionalizing the surface of the particle obtained following the steps 1) to 3) with affinity recognition for selectively binding with a target molecule.

This method of the first aspect of the invention preferably further comprises a step of adding a shell material in coexistence with the ferromagnetic phase material, i.e. advantageously the aforesaid fine ferromagnetic having zero coercive field or a given coercive field, in contact with the shell material. The shell materials can be chosen either among an antiferromagnetic material, a ferromagnetic magnetic of a kind different from the core ferromagnetic material or a metal material. By a proper choice of materials and dimension tuning of both the core and the shell as well as the amount and the concentration of the magnetic elements within the non-magnetic matrix, the biofunctionalized magnetic particles is tailored to exhibit an enhanced magnetic energy. In the case of the using an antiferromagnetic material shell, the Néel temperature of the antiferromagnetic phase is not less than 300 K. Further, the ferromagnetic material phase and the antiferromagnetic phase are in a state to minimize the magnetic exchange bias coupling field (ft) and to provide a specific coercive field $_{(I-L)}$. More specifically, it is preferable that the magnetic exchange bias coupling field is lower than the coercive field, ($H_e<H_c$). Several antiferromagnetic phase materials can be used, such as, but not limited to, ferromagnetic oxide like NiO and several alloys like NiMn and FeMn.

It is important to point out that the particles prepared according to the method of the invention are substantially unmagnetized and preferably completely unmagnetized. Indeed, even composed from "permanently" magnetized primary fine particles the prepared secondary particle is substantially unmagnetized due to the random distribution of the magnetization of the fine primary particles within the non-magnetic matrix. However, the application of an external magnetic will align the magnetization of the primary fine particles along the applied field, leading therefore to the magnetization of the composed secondary particle. The secondary particle will acquire a permanent magnetic moment with a predefined coercive field that is controlled by adjusting the coercive field, the amount and the concentration of the primary fine particles within the non-magnetic matrix.

To obtain the first aspect of the invention, the non-magnetic material forming notably the core of the secondary magnetic particles is preferably a polymeric material, silica or glass.

The steps of preparing magnetic particles according to the first aspect of the invention preferably further comprise a heat annealing step to adjust and enhance the coercive field the secondary particles.

The resulting magnetic particles present the advantage of have a rapid magnetic response even at low applied magnetic field. Moreover, contrary to the particles described in the prior art, the particles of the present invention take benefit from the "residual" magnetisation through the control of the magnetic hysteresis loss of the particle when the particles are manipulated with an alternating magnetic field.

A method of manipulating magnetic particles according to the second aspect of the invention comprises the following steps:
1. Providing a suspension of substantially unmagnetized magnetic particles and that present a hysteretic response with a specific coercive field in the presence of an external magnetic field;
2. Introducing an amount of the said magnetic particles suspension in a manipulation cell;
3. Applying a static magnetic field to cause magnetic particles aggregation structures;
4. Applying an alternating magnetic field to cause angular rotation of the magnetic chain aggregation structures in response to the field alternation;
5. Adjusting the amplitude and the frequency of the alternating magnetic field to break down the particles aggregation structure and thereby advantageously control the aggregation length of the particles.

Moreover in the second aspect of the invention, the method preferably further comprises a step of adding to the alternating/oscillating magnetic field a direct "positive" magnetic field component whose amplitude is equal to the magnetic exchange bias field. In this method the particles preferably have a coercive field greater than or close to the amplitude of the applied alternating magnetic field.

A method of using the magnetic particles according to the third aspect of the invention comprises contacting the magnetic particles obtained following the first aspect of the invention with a carrier fluid (usually containing samples to be processed for life science and chemical assays) and then manipulating the particles following the second aspect of the invention.

Accordingly, the third aspect of the invention disclose a suspension that contains magnetic particles designed to respond with a defined magnetic coercive field to an external magnetic field. The surfaces of the said magnetic particles are specifically functionalized with affinity recognition group for selectively binding with target molecules. The said suspension is a part of a kit that includes other reagents required for assaying, manipulation and purification of biomolecules and chemical substances.

Regarding the final goal of the invention, the third aspect of the invention disclose a suspension that contains bio-functionalized magnetic particles designed to respond with a defined magnetic coercive field to the application of an external magnetic field. The surfaces of the said magnetic particles are specifically functionalized with affinity recognition group for selectively binding with target molecules. To fit the invention requirements, the magnetic particles are prepared to be unmagnetized before their use or manipulation using an external magnetic field. Instead, the particles will develop a controlled hysteretic response characterized by a specific coercive field when subjected to an external magnetic field. Contrary to the particles available on the market, which are designed to exhibit superparamagnetic behavior, the particles according the invention have a "large coercive field". The required coercive field is between 100 to 20,000 Oe and preferably between 200 to 1000 Oe. To reach such high coercive field values the suspension is prepared following the first aspect of the invention. The said suspension is a part of a kit that includes other reagents required for assaying, manipulation and purification of biomolecules and chemical substances. To accomplish these objectives the magnetic particles are manipulated following the second aspect of the invention.

BRIEF DESCRIPTION OF THE DRAWINGS

In the accompanying schematic drawings, given by way of example:

FIGS. 1 (*a*) (*b*) and (*c*) are cross sectional views of three magnetically responsive particles according to the first embodiment realising the first aspect of the invention.

FIGS. 7(*a*) and 7(*b*) graphically illustrate a step in the second aspect of the invention involving adding to an oscillating magnetic field a direct "positive" magnetic field component whose amplitude is equal to the magnetic exchange bias coupling field.

FIG. 7(*c*) is a schematic view illustrating the behaviour of magnetic particle chains during their manipulation with an alternating magnetic field combined with a lateral driving force.

DETAILED DESCRIPTION OF THE PREFERRED EMBODIMENTS

Figure 1:
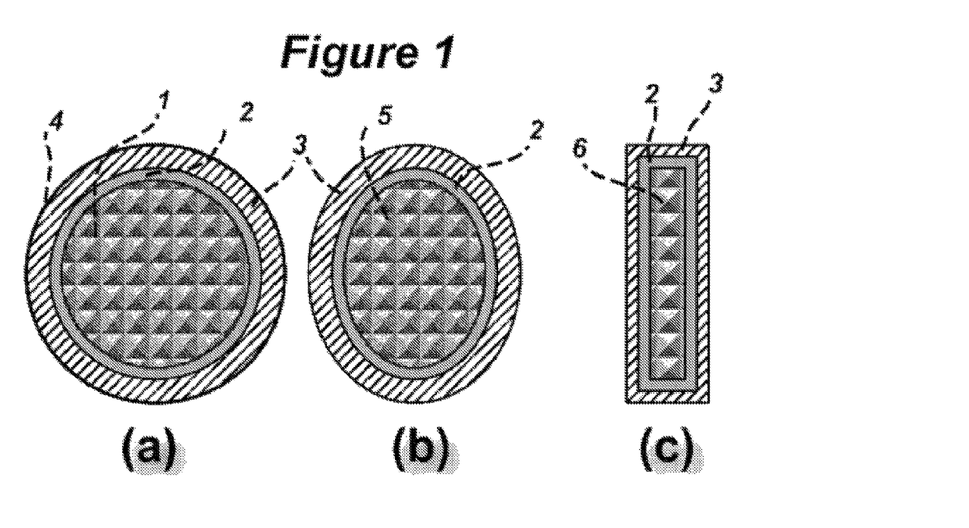

To obtain the first aspect of the invention, according to the first embodiment of the invention (as shown in FIG. 1), primary fine magnetic particles are composed from a ferromagnetic material particle core (1) coated with a fine shell material (2). The shell materials can be chosen either among antiferromagnetic material, a ferromagnetic magnetic of a kind different from the core ferromagnetic material or transition metal material. In the case of an antiferromagnetic material shell, the Néel temperature of the antiferromagnetic phase is not less than 300 K. This primary fine particle is encapsulated in a non-magnetic material matrix (3). Preferably such matrix material is a polymer, silica or glass. The surface (4) of the so-formed secondary magnetic responsive particle is biochemically functionalised by specific ligands for the probing and manipulating of biomolecules and chemical substances using well-known techniques. For this, the magnetic particle surface comprises for example a functional group or a ligand that is capable of binding to a target molecule or to class of target molecules. Potential functional groups comprise but are not limited to carboxylic acids, hydroxamic acids, nonadhesive compounds, amines, isocyanates, and cyanides. Potential ligands comprise but are not limited to proteins, DNA, RNA, enzymes, hydrophobic materials, hydrophilic material, and antibodies. More generally, examples of ligands suitable for use in the present invention include, but are not limited to, molecules and macromolecules such as proteins and fragments of proteins, peptides and polypeptides, antibodies, receptors, aptamers, enzymes, substrates, substrate analogs, ribozymes, structural proteins, nucleic acids such as DNA and RNA and DNA/RNA hybrids, saccharides, lipids, various hydrophobic or hydrophillic substances, lipophilic materials, chemoattractants, enzymes, hormones, fibronectin. and the like. Such molecules and macromolecules may be naturally occurring or synthetic. The term ligand may also include larger entities such as cells, tissues, entire microorganisms, viruses, etc.

The size of the fine ferromagnetic core (1) determines the magnetic response of the particles, and is preferably less than the size of a single magnetic domain. Particles with diameter larger than a magnetic domain contain a plurality of magnetic domains. In this case, larger energy in required to reverse the magnetisation of the particles which in turn appear in a lower coercive field. On the other hand, as the dimension of the particles becomes smaller, the particles' magnetisation becomes all the more susceptible to thermal fluctuation. To enhance the coercive field of the particles while maintaining their fine size, the ferromagnetic core (1) of the particle is coated with the thin specific material layer (2). Indeed, the magnetic exchange in the interface between the ferromagnetic core (1) and thin layer (2) will considerably increase the anisotropy energy and therefore the coercive field. In this case, by increasing the thickness of the shell (2) one can consequently increase the coercive field. However, in the case of an antiferromagnetic material there is an upper limit of the thickness of the antiferromagnetic shell (2) above which the magnetic exchange bias coupling with the ferromagnetic core becomes effective leading to a shifting of the hysteresis curve and therefore a minimisation of the hysteresis loss.

To enhance the coercive field of the fine particles while maintaining their fine size, the ferromagnetic core is preferably acicular (FIG. 1(c)) to increase the shape anisotropy compared with a spherical core (FIG. 1(a)) or, to a lesser extent, with a generally oval or oblong one (FIG. 1(b)). In these Figures, references 1, 5 and 6 indicate the ferromagnetic core which is preferably a single-domain core. To enhance the coercive field of a multi-domain particle, it is possible to add a shell material around the multi-domain ferromagnetic core. However, it is preferable that the particle is a single-domain particle (fine particle). The mean diameter (or cross-dimension) of a single domain particle is generally less than 200 nm and preferably less than 25 nm.

Figure 2:
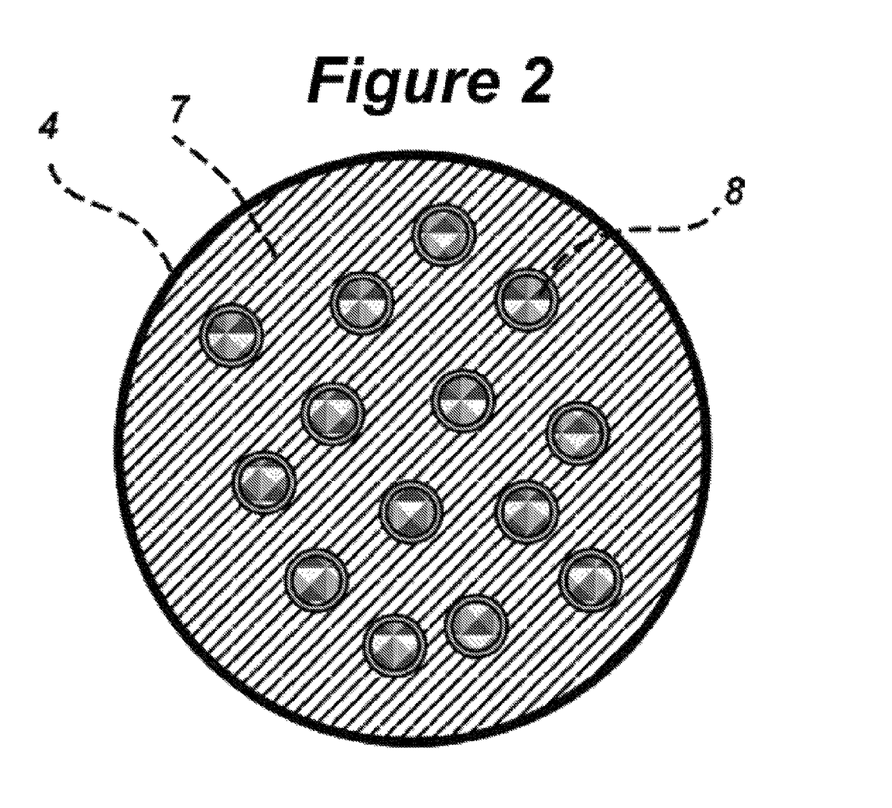
FIG. 2 is a cross sectional view of a magnetically responsive particle according to a second embodiment realising the first aspect of the invention.

In a second embodiment of the first aspect of the invention (shown in FIG. 2), secondary magnetically responsive particles are obtained by encapsulating at least one of the primary fine magnetic particles (8) in particular of the kind described above in connection with FIG. 1 in a non-magnetic material matrix (7). The amount, the size and the distribution within the matrix (7) of the primary fine particles (8) determine the entire magnetic proprieties of the final particle. More specifically, the coercive field of the particle is set by adjusting first the coercive field of fine primary particles components and secondly by adjusting the size and the concentration of the fine particles (8) within the matrix (7). The surface (4) of the so-formed secondary magnetic responsive particle is biochemically functionalised, for example as described above.

Figure 3:
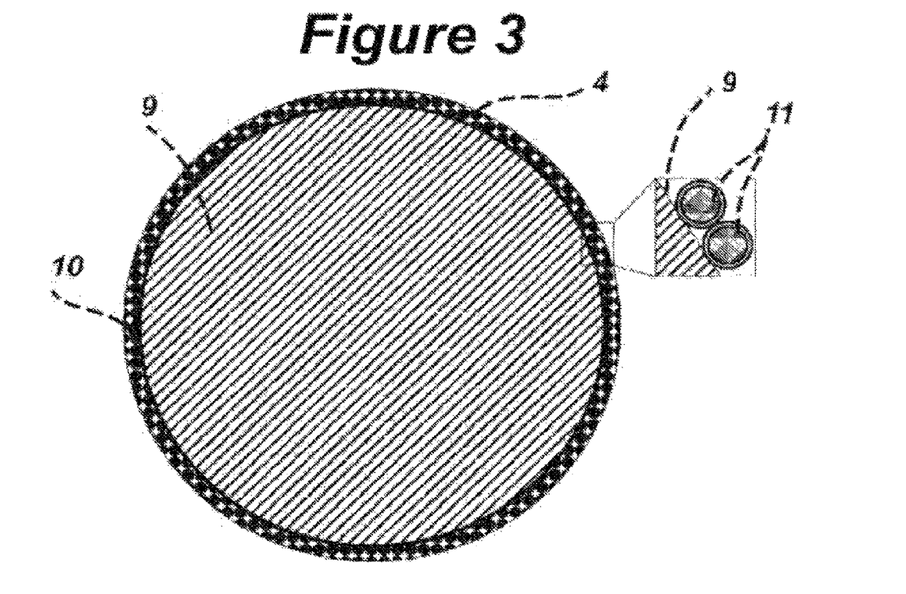
FIG. 3 is a cross sectional view of a magnetically responsive particle according to a third embodiment realising the first aspect of the invention, with a detail shown in enlargement.

A third embodiment of the first aspect of the invention (shown in FIG. 3), consists of secondary magnetically responsive particles obtained by the deposition of a layer (10) of primary fine magnetic particles (11) in particular of the kind described above in connection with FIG. 1 on nonmagnetic material bead (9). The thickness of the deposited layer (10), the concentration and the size of the primary fine particles (11) within the layer (10) determine the entire magnetic proprieties of the secondary particles. More specifically, the coercive field of the secondary particle is set by adjusting first the coercive field of the deposited fine particles (11) and secondly by adjusting the size of the ferromagnetic core (1,5, 6), the amount and concentration of the particles (11) within the layer (10) and the thickness of the layer (10).

Figure 4:
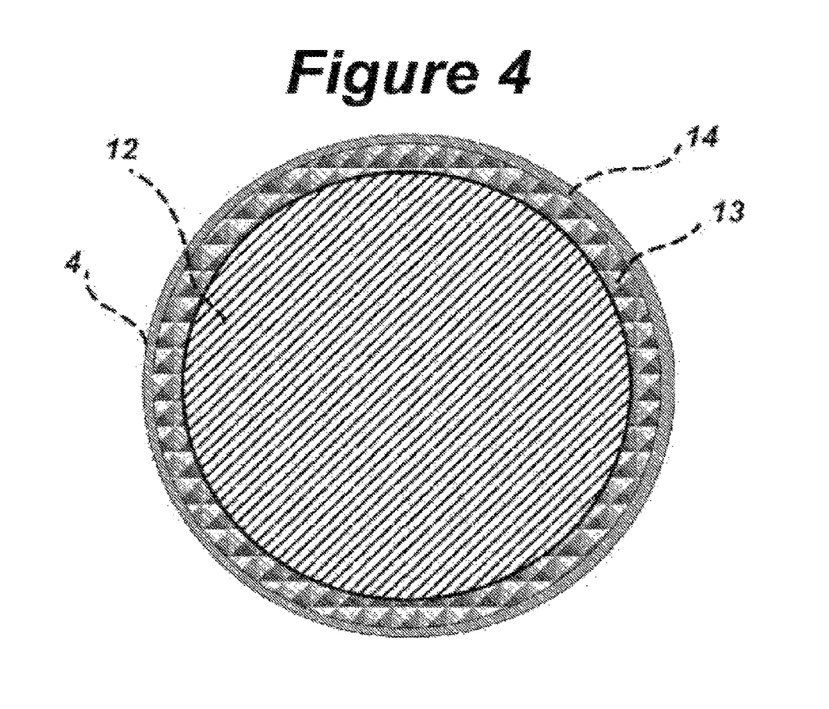
FIG. 4 is a cross sectional view of a magnetically responsive particle according to a fourth embodiment realising the first aspect of the invention.

In a fourth embodiment of the first aspect of the invention (shown in FIG. 4), secondary magnetically responsive particles are obtained by the deposition on a nonmagnetic bead (12), of a first layer composed of ferromagnetic fine particles (13) followed by a deposition of a second outer shell composed of specific material fine particles (14), also in particular the shell materials can be chosen either among antiferromagnetic material, a ferromagnetic material of a kind different from the core ferromagnetic material or a transition metal material. In the case of an antiferromagnetic shell, the Néel temperature of the antiferromagnetic fine particle phase is not less than 300 K. The thickness of the ferromagnetic layer and the specific material shell determines respectively the magnetic response and the coercive field of the secondary particles. However, in the case of an antiferromagnetic material, the thickness of the antiferromagnetic shell (14) is controlled to minimize the magnetic bias field. For this, its thickness is lower than the limit above which magnetic exchange field coupling with the ferromagnetic layer becomes effective. Other factors that can contribute effectively to the magnetic properties of the secondary particle are the size, shape and the concentration of the primary ferromagnetic particles (13) forming the first ferromagnetic layer.

Figure 5:
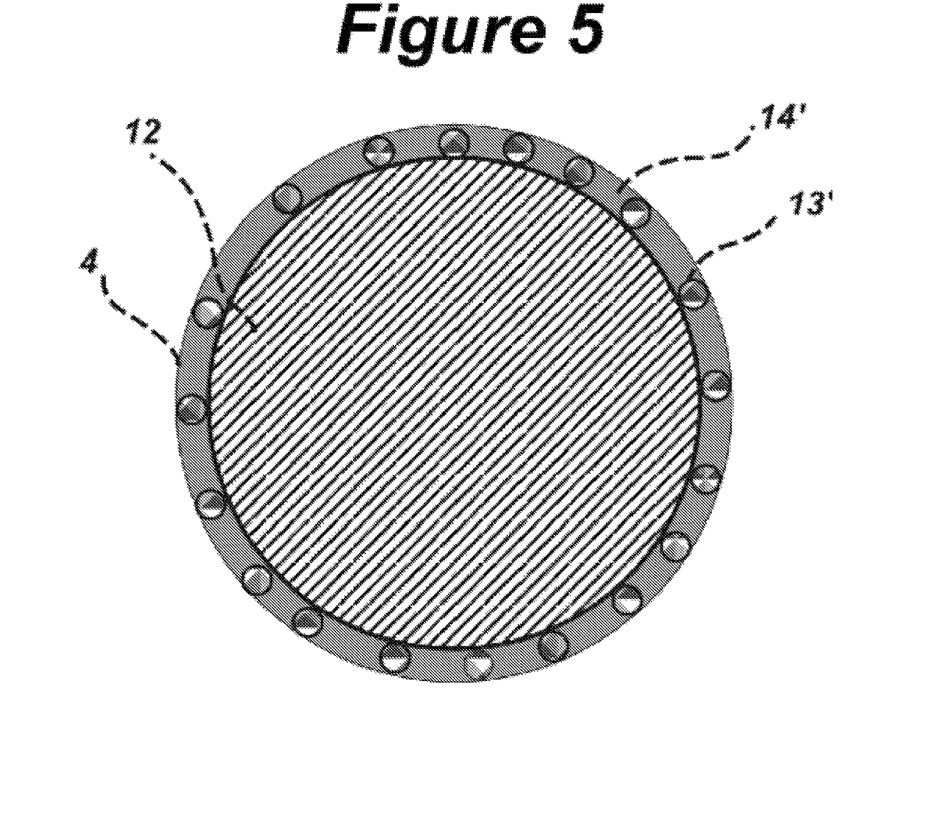
FIG. 5 is a cross sectional view of a magnetically responsive particle according to a fifth embodiment realising the first aspect of the invention.

In the fifth embodiment of the first aspect of the invention (shown in FIG. 5), secondary magnetically responsive particles are obtained by the deposition, on the surface of a non-magnetic bead (12), of a specific material fine particle layer (14') in which a quantity of primary fine ferromagnetic particles (13') are uniformly dispersed. The specific shell material can be chosen either among antiferromagnetic material, a ferromagnetic material of a kind different from the core ferromagnetic material or a transition metal material. The ferromagnetic particles (13') are in particular of the kind described above in connection with FIG. 1. In this case one can consider that the layer (14') forms a matrix in which the primary ferromagnetic fine particles (13') are dispersed. The thickness of the layer (14') and the concentration of the fine ferromagnetic particles (13') dispersed therein are controlled to provide a specific coercive field of the secondary particles.

Accordingly, in the step of preparing the magnetic particles according to the invention a heat annealing step is preferred to adjust and increase the coercive field the secondary particles. For instance, to fit the requirements of the invention magnetic fine particles with large magnetic anisotropy such as FePt are required. However, usually the FePt fine particles are provided as a ferrofluid suspension with a disordered fcc FePt crystalline structure. Such structure has low anisotropy and hence needs to be thermally annealed in order to obtain the fct phase with high uniaxial magnetocrystalline anisotropy responsible for the high coercive field. Heating at 600° will lead to an increasing of the coercive field for larger values that can reach thousands of Oe. Moreover, to resist to the high heating temperature requirement the fine particles are preferably dispersed in a non-magnetic matrix having large melting temperature such as glass.

The thermal annealing step is particularly required when the particles according to the invention are synthesized starting from a ferrofluid suspension of supraparamagnetic nanoparticles. In this condition, the ferrofluid is composed from nanoparticles with low crystalline magnetic anisotropy such as disordered or amorphous crystalline structures. After the integration of the nanoparticles in a non-magnetic matrix, a heating step is used to adjust the nanocrystals structure and provide the resulting secondary particles with larger magnetocrystalline anisotropy.

Figure 6:
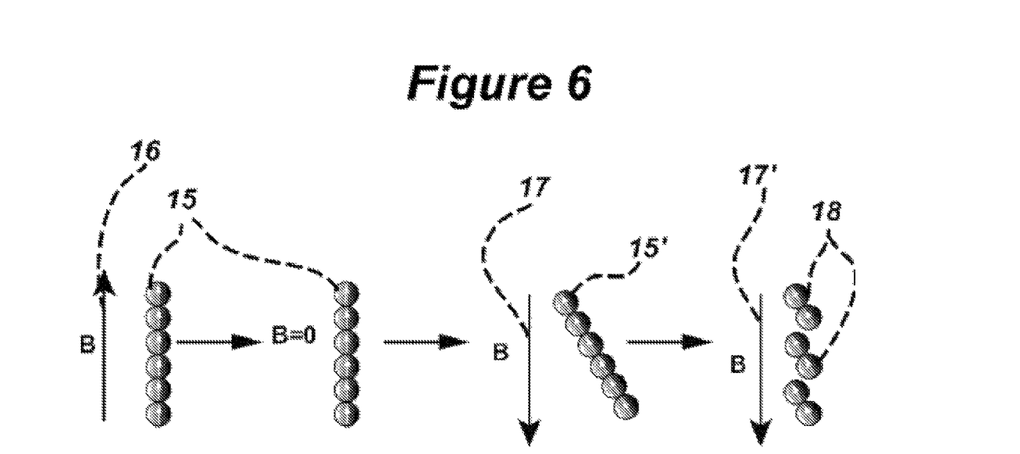
FIG. 6 is a schematic view illustrating the behaviour of magnetic particle chains during their manipulation with an alternating magnetic field.

Turning to the second aspect of the invention, a suspension of the magnetic particles synthesized in particular following the first aspect of the invention is introduced in a cell in which the particles will be manipulated using an external magnetic field. As shown in FIG. 6, under the influence of the magnetic field the particles will develop a magnetic moment in the direction of the applied field B (16). Due to their mutual magnetic dipole interaction, the individual particles align to form longer magnetic chain structures (15). Contrary to the case of supraparamagnetic material, even if the external magnetic field is removed or turned off, the magnetic chain structures (1 5) remain intact in the case where the particles used are those provided by the first aspect of the invention. In this case, when switching the polarity of the applied magnetic field (17) as illustrated in the middle of FIG. 6, the field-oriented and aggregated magnetic dipoles (15) will tend to follow the changing magnetic field polarity and will start to rotate. During this rotational process, a viscous torque, arising from rotational friction of the structures in the suspending fluid, will act on the aggregates and tend to prevent the chain from rotating. If the applied magnetic field (1 7) switches continually (alternating field) with a given frequency and in order to minimize the total viscous energy, the magnetic chains will break up into more open and smaller size structures (18). This breaking up process illustrated in the right-hand part of FIG. 6, is more pronounced at higher frequencies of the alternating field.

Therefore, a main feature of the second aspect of the invention consists in the manipulation of the magnetic aggregations by an alternating magnetic field to control the aggregation length. The higher the external magnetic field alternation frequency, the lower is the resulting reduced aggregation length. The "ideal extreme" state is reached when the smallest magnetic aggregation length is equal to the magnetic particle size, which obviously implies the application of a high frequency alternating magnetic field. As the field frequency becomes higher, the magnetic chain aggregations do not have enough time to follow the field alternations, which impose the use of magnetic particles with higher coercive field to reach lower aggregated particles state.

Two physical characteristics of the magnetic particles are important in the manipulation of magnetic chain aggregations using an alternating magnetic field: the magnetic remanence and the coercive field. The higher these values, the higher the frequencies at which the magnetic chain aggregations can rotate. Moreover, to minimize the agglomeration of the magnetic particles under the application of an external alternating magnetic field, the coercive field of the particles is preferably greater or at least close to the amplitude of applied field. Increasing the hysteresis loss of the magnetic particles is, therefore, a main feature of manipulating magnetic particles using an alternating magnetic field.

To reach the mean objective of the second aspect of the invention the magnetic particles are preferably realized following the first aspect of the invention. Moreover, the particles are preferably spherical and substantially monodispersed in size and magnetic proprieties. Instead, according to the second aspect of the invention the particles diameter is in the range of 10 nm to 100 μm, with dispersion that must be less than 30% and more preferably less than 10%. Accordingly, the dispersion of the magnetic content of the particles (concentration of the fine particles within the matrix) is less than 30% and more preferably less than 10%.

Accordingly, to reach the mean objective of the second aspect of the invention the magnetic particles are realized with a defined coercive field of the particles following the first aspect of the invention so that the smallest magnetic aggregation length is equal to the magnetic particle diameter. This fully disaggregated state is more preferably reached with particles that present a coercive field that is greater than or close to the amplitude of the applied alternating magnetic filed. Moreover, this state is preferably reached for magnetic field anplitudes in the range of 0.01 Tesla to 1 Tesla and a field alternation frequency in the range of 0.1 Hz to 200 Hz.

Figure 7A:
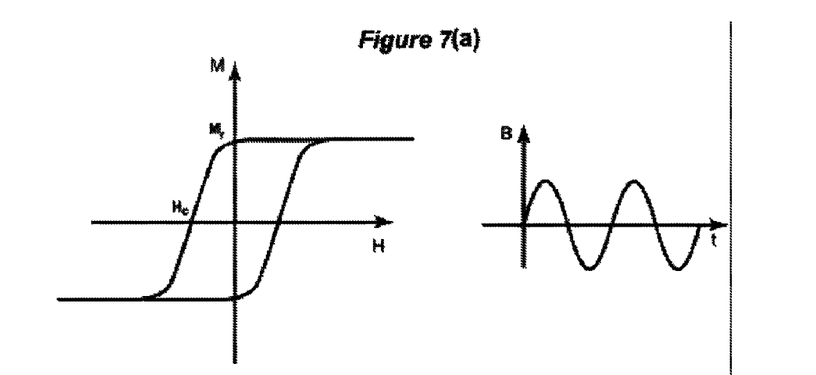
Figure 7B:
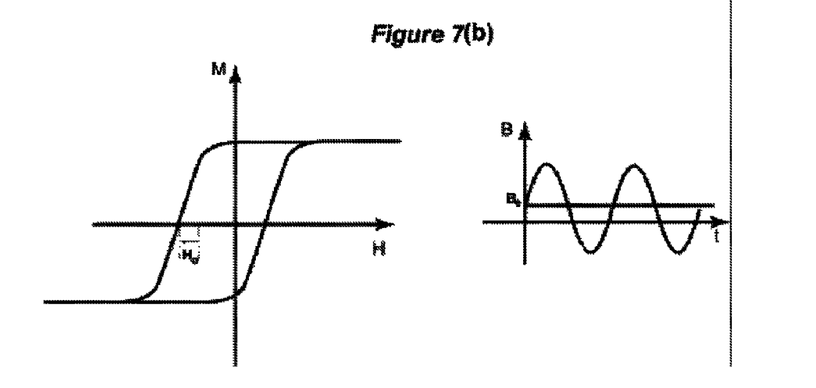

FIGS. 7(a) and 7(b) graphically illustrate a step in the second aspect of the invention involving adding to an oscillating magnetic field a direct "positive" magnetic field component whose amplitude is equal to the magnetic exchange bias coupling field. When a ferromagnetic material is contacted with an antiferromagnetic material, for example as described above in connection with FIG. 1, the exchange interaction between the two materials will induce an enhancement of the coercive field (I-t) as shown in the left of FIG. 7(a). Moreover, a "negative" shifting of the hysteresis loop along the field axis (the bias exchange field He) can also be induced, as shown in the left of FIG. 7(b). The latter leads to a dissymmetry of the hysteresis loop which becomes non-centralized around zero. The invention aims to maximize the hysterisis loss when the particles are manipulated with an alternating magnetic field. To achieve this, the induced bias dissymmetry must be small compared to the coercive field. Moreover, even if a significant bias field is induced it is possible to compensate the induced dissymmetry by manipulating the particles with a "positively" shifted oscillating magnetic field as schematically shown in the right of FIG. 7(b). This can be done simply by adding a direct magnetic field component ($B_e$) having an amplitude equal to the magnetic bias coupling field.

Figure 7C:
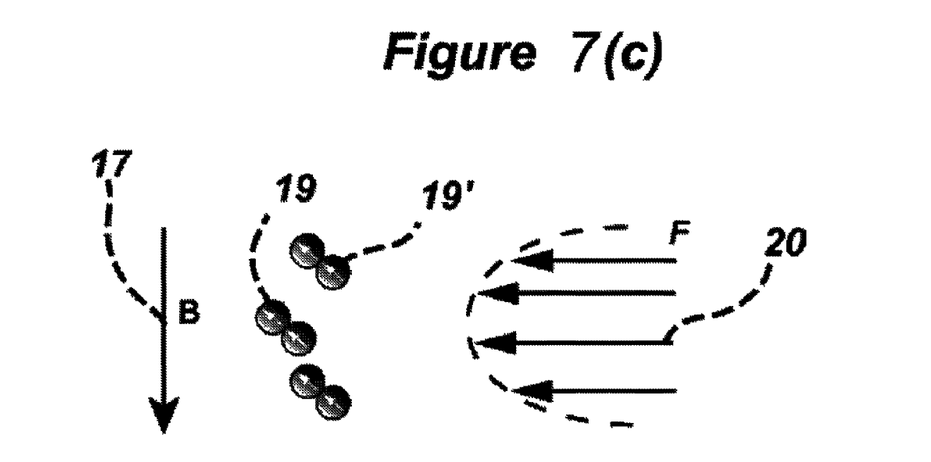

Another main feature of the second aspect of the invention (as shown in FIG. 7(c)) consists in the manipulation of magnetic particle chain aggregations using an alternating magnetic field (17) while at the same time the magnetic particle chain aggregations are subjected to a transverse external force field F (20). In practice, the fields (17) and (20) are not uniform whereby the smaller magnetic chain aggregations (19) and (19') are not subjected to same forces leading, thus, to less aggregated magnetic chain structures. In one embodiment, the external transverse force F is a magnetic gradient force and in another embodiment the external transverse force is a flow drag force.

Figure 8:
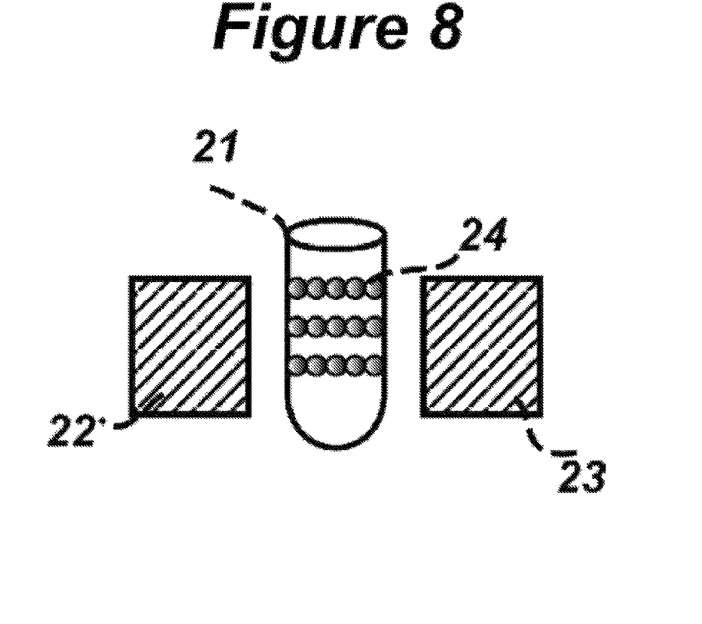
FIG. 8 is a schematic view illustrating the manipulation of magnetic particle chain aggregation structures using an alternating magnetic field in a test tube according to a sixth embodiment realising the second aspect of the invention.

In a sixth embodiment of the invention according to its second aspect (as shown in FIG. 8), an amount of magnetic particles synthesized in particular following the first aspect of the invention is suspended in a test tube (21) between two magnetic poles (22,23). A static magnetic field is first applied covering the whole test tube volume to cause the formation of magnetic chain aggregation structures (24). Preferably the amount of the magnetic particles used is such that each particle chain aggregation (24) covers uniformly the test tube volume. An alternating magnetic field is then applied to cause a rotation of the magnetic chains in response to the field alternation. By adjusting the magnetic field amplitude and alternation frequency one can control the maximum magnetic chain length within the aggregations. The small magnetic chain rotation dynamics serves to mix the magnetic particles with the surrounding liquid medium.

Figure 9:
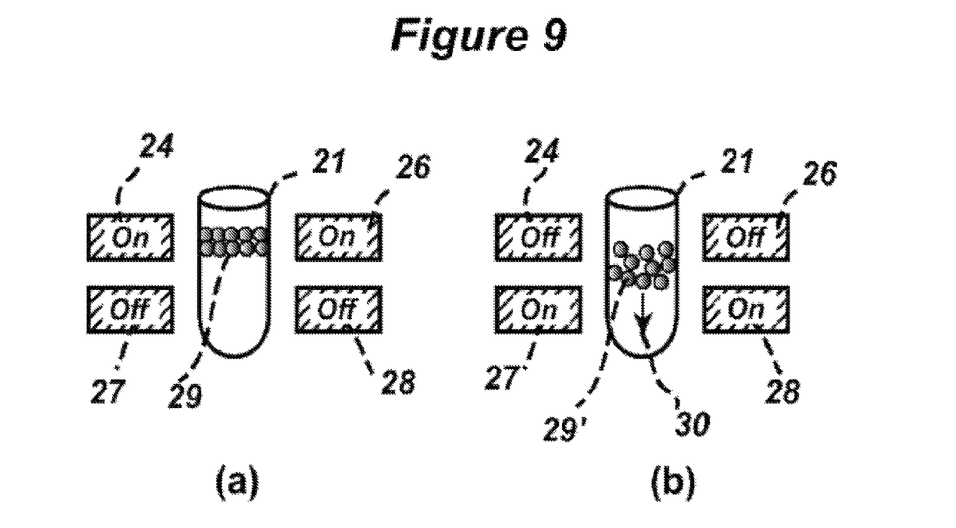
FIG. 9 is a schematic view illustrating the manipulation of magnetic particles according to a seventh embodiment realising the second aspect of the invention, wherein magnetic chain aggregation structures are manipulated by an alternating magnetic field and transported along a test tube with a travelled magnetic field gradient.

In a seventh embodiment of the invention in its second aspect (as shown in FIG. 9), as in the sixth embodiment, an amount of magnetic particles synthesized in particular following the first aspect of the invention is suspended in a test tube (21). The difference consists in the use of two couples of magnetic poles (24, 26) and (27, 28). The magnetic field generated from the first magnetic pole couple (24, 26) covers at least the upper half of the test tube volume while the second magnetic pole couple (24, 26) covers the remaining lower half of the test tube volume. A spatial overlap of the magnetic field generated by the two magnetic pole couples is a necessary condition in the functioning of the system. First, as shown in the left hand part of FIG. 9, while the pole couple (27,28) remains unactuated, the magnetic pole couple (24,26) is actuated which results in the formation of magnetic chain aggregations (29). The amount of the magnetic particles used is such that the magnetic chain aggregations (29) form a dense structure substantially covering the test tube cross section. As in the sixth embodiment, the aggregation length is controlled by adjusting the magnetic field amplitude and alternation frequency. In a second step, illustrated in the right hand part of FIG. 9, the magnetic pole couple (24, 26) is turned off while the second magnetic pole couple (27,28) is actuated with an alternating magnetic field. The magnetic chain aggregation structure (29') will be attracted by the magnetic field gradient (30) generated by the pole couple (27, 28) and so transported along the test tube (21) from the upper volume space to the lower volume space. Since the magnetic field gradient force (30) generated by pole couple (27, 28) is not uniform, the small chain aggregations are not subjected to the same force, which leads to less-aggregated magnetic chain structures (29') during the transportation process.

According to the third aspect of the invention, a method is provided which consists in the use of a fluid suspension of the magnetic particles obtained following the first aspect of the invention and manipulated following the second and the third aspects of the invention in live science applications and particularly for assaying, manipulation and purification of biomolecules and chemical substances.

Accordingly, the third aspect of the invention discloses a suspension that contains magnetic particles designed to respond with a defined magnetic coercive field to an external magnetic field. The surfaces of the said magnetic particles are specifically functionalized with affinity recognition group for selectively binding with target molecules. The said suspension is a part of a kit that includes other reagents required for assaying, manipulation and purification of biomolecules and chemical substances.

While the present invention has been described through particular illustrative embodiments, it is not to be restricted by those embodiments but only by the appended claims. Accordingly, the invention will include any changes, modifications or combinations of the embodiments without departing from the scope of the invention.

The invention claimed is:

1. Bio-chemically active magnetic particle for use in a magnetic particle fluid suspension for selectively binding with at least one target molecule, the particle comprising:
    a) a non-magnetic component;
    b) a magnetic core/shell component comprising a ferromagnetic core material and a shell material, the ferromagnetic material comprising at least one fine ferromagnetic particle having zero coercive field or a given coercive field, the fine ferromagnetic particle(s) being associated with the shell material phase to provide a coercive field greater than that of the fine ferromagnetic particle(s); and
    c) an external coating designed to allow an affinity recognition for selectively binding the particle with at least one target molecule;
        wherein the shell material can be chosen either among an antiferromagnetic material, a ferromagnetic material of a kind different from the core ferromagnetic material, a transition metal or a metal oxide material; and
        wherein the Néel temperature of the antiferromagnetic phase is above 300 K.

2. Particle according to claim 1 consisting of a core made of the ferromagnetic material coated with a shell material, both materials forming said magnetic component, said non-magnetic component encapsulating said magnetic component.

3. Particle according to claim 1 comprising a plurality of said magnetic components, each consisting of a core of the ferromagnetic material coated with shell material, said magnetic components being embedded in said non-magnetic component.

4. Particle according to claim 1 comprising a core made of said non-magnetic component coated by a layer consisting of a plurality of said magnetic components, each magnetic component consisting of a core of the ferromagnetic material coated with shell material.

5. Particle according to claim 1 wherein the magnetic component comprises a core made of said non-magnetic component coated by a first layer consisting of the ferromagnetic material and a second fine layer consisting of the shell material.

6. Particle according to claim 1 comprising a core made of said non-magnetic component coated with a layer of shell material in which a plurality of ferromagnetic elements are embedded.

7. Particle according to claim 1 wherein the ferromagnetic core material is a transition metal material.

8. Particle according to claim 1 wherein the shell material forms a layer whose thickness gives a specific coercive field.

9. A kit containing magnetic particles according to claim 1, and reagents for assaying, manipulating or purifying biomolecules or chemical substances.

10. A method of preparing magnetic particles with a defined coercive field that comprises the steps of:
    a) Providing primary magnetic responsive ferromagnetic particles comprising a ferromagnetic core material and a shell material, the ferromagnetic material comprising at least one fine ferromagnetic particle having zero coercive field or a given coercive field above 300 K, the said fine ferromagnetic particle or particles being associated with a shell magnetic material phase to provide a coercive field mush greater than that of the fine ferromagnetic particles;
    b) Integrating the primary ferromagnetic particles of step a) in a non-magnetic support to provide a secondary core particle;
    c) Adjusting the coercive field of the secondary particle by controlling the amount and the concentration of the primary ferromagnetic particles provided in step a) and integrated following step b); and
    d) Functionalizing the surface of the particle obtained following the steps a) to c) with affinity recognition for selectively binding with a target molecule,
        wherein the particles prepared by steps a) to c) are prepared to be substantially unmagnetized before their use or manipulation using an external magnetic field;

wherein the shell material can be chosen either among an antiferromagnetic material, a ferromagnetic material of a kind different from the core ferromagnetic material, a transition metal or a metal oxide material; and wherein the Néel temperature of the antiferromagnetic phase is above 300 K.

11. A method according to claim 10 which further comprises a thermal annealing step to adjust the coercive field of the secondary core particle.

12. A method according to claim 10 wherein the coercive field of the particles produced by steps a) to c) of claim 10 is between 100 to 20,000 Oe.

13. A method according to claim 12 wherein the coercive field of the particles produced by steps a) to c) of claim 10 is between 200 to 1000 Oe.

14. A method according to claim 10 wherein the fine ferromagnetic particle or particles provided in step a) of claim 10 have a size between 1 to 500 nm.

15. A method according to claim 14 wherein the fine ferromagnetic particle or particles provided in step a) of claim 10 have a size between 5 to 50 nm.

16. A kit containing magnetic particles prepared by the method of claim 10, and reagents for assaying, manipulating or purifying biomolecules or chemical substances.

* * * * *